United States Patent [19]

Lane et al.

[11] Patent Number: 4,775,360

[45] Date of Patent: Oct. 4, 1988

[54] AUTOLOGUS BLOOD METHODS AND APPARATUS

[75] Inventors: Perry L. Lane; William D. Wallace, both of Salt Lake City, Utah

[73] Assignee: Lantech, Inc., Salt Lake City, Utah

[21] Appl. No.: 1,584

[22] Filed: Jan. 9, 1987

Related U.S. Application Data

[63] Continuation-in-part of Ser. No. 928,928, Nov. 7, 1986.

[51] Int. Cl.$^4$ .................................. A61M 37/00
[52] U.S. Cl. ........................... 604/4; 604/119; 604/283; 604/284; 604/319; 604/322; 128/767; 55/159
[58] Field of Search .................. 604/4–6, 604/317–326, 35, 49–52, 119, 131, 133, 149, 902, 905, 280, 283, 284, 406, 80, 83, 268, 269, 121, 122, 126; 128/760, 762, 767, DIG. 3; 55/178, 185, 199, 260, 434, 437, 462, 532, 159

[56] References Cited

U.S. PATENT DOCUMENTS

| | | | |
|---|---|---|---|
| 3,191,600 | 6/1965 | Everett | 604/268 |
| 3,680,560 | 8/1972 | Pannier, Jr. et al. | 128/276 |
| 3,685,517 | 8/1972 | Reynolds et al. | 128/277 |
| 3,704,709 | 12/1972 | Sorenson et al. | 128/277 |
| 3,849,071 | 11/1974 | Kayser | 55/216 |
| 3,863,634 | 2/1975 | Reynolds et al. | 128/276 |
| 3,866,608 | 2/1975 | Reynolds et al. | 128/276 |
| 4,006,745 | 2/1977 | Sorenson et al. | 604/4 |
| 4,014,329 | 3/1977 | Welch et al. | 128/214 R |
| 4,047,526 | 9/1977 | Reynolds et al. | 128/214 R |
| 4,368,118 | 1/1983 | Siposs | 55/178 |
| 4,424,053 | 1/1984 | Kurtz et al. | 604/4 |
| 4,428,743 | 1/1984 | Heck | 604/122 |
| 4,435,170 | 3/1984 | Laszczower | 604/4 |
| 4,443,220 | 4/1984 | Hauer et al. | 604/400 |
| 4,466,888 | 8/1984 | Verkaart | 604/406 |
| 4,493,705 | 1/1985 | Gordon et al. | 60/122 |
| 4,500,308 | 2/1985 | Kurtz et al. | 604/4 |
| 4,540,406 | 9/1985 | Miles | 604/269 |
| 4,547,186 | 10/1985 | Bartlett | 604/4 |
| 4,643,713 | 2/1987 | Viitala | 604/122 |

OTHER PUBLICATIONS

Schaff et al., "Routine Use of Autotransfusion Following Cardiac Surgery: Experience in 700 Patients," 27 Annals of Thoracic Surgery, 493 (Jun. 1979).

Thurer et al., "Autotransfusion Following Cardiac Operations: A Randomized, Prospective Study," 27 Annals of Thoracic Surgery, 500 (Jun. 1979).

Bell, "The Hematology of Autotransfusion," 84 Surgery, 695 (Nov. 1978).

Council on Scientific Affairs, "Autologous Blood Transfusion," 256 JAMA, No. 17 (Nov. 1986).

Johnson et al., "The Efficacy of Postoperative Autotransfusion in Patients Undergoing Cardiac Operations,:" 36 Annals of Thoracic Surgery, 173 (Aug. 1983).

"Pleur-Evac Autotransfusion System" Product Brochure.

Hower, "Autotransfusions," 300 New England Journal of Medicine at 1276 (May 1979).

Cordell et al., "An Appraisal of Blood Salvage Techniques in Vascular and Cardiac Operations," 31 Annals of Thoracic Surgery, 421 (May 1981).

Voegele et al., "An Improved Method for Collection of Shed Mediastinal Blood for Autotransfusion," 32 Annals of Thoracic Surgery, 471.

Primary Examiner—John D. Yasko
Assistant Examiner—Mario Costantino
Attorney, Agent, or Firm—Workman, Nydegger & Jensen

[57] ABSTRACT

The present invention is directed to improved methods and apparatus for the collection of blood, which are particularly useful for autotransfusion purposes. The apparatus includes a conventional blood transfer bag which is in turn placed in fluid communication with an air-blood separator to form a collection system. This system is particularly adaptable for use in the surgical setting in that it can operate at high vacuum while minimizing hemolysis. This is accomplished by early separation of air from the blood as the blood is collected.

The air-blood separator and the interior of the blood bag are placed in communication with a vacuum source. As a result, there is a pressure equalizing feature inherent within the device. This allows the blood to continue to flow through the device into the blood bag without extending or opening the blood bag. As a result, there is minimal air-blood interface as the blood enters the blood bag.

24 Claims, 4 Drawing Sheets

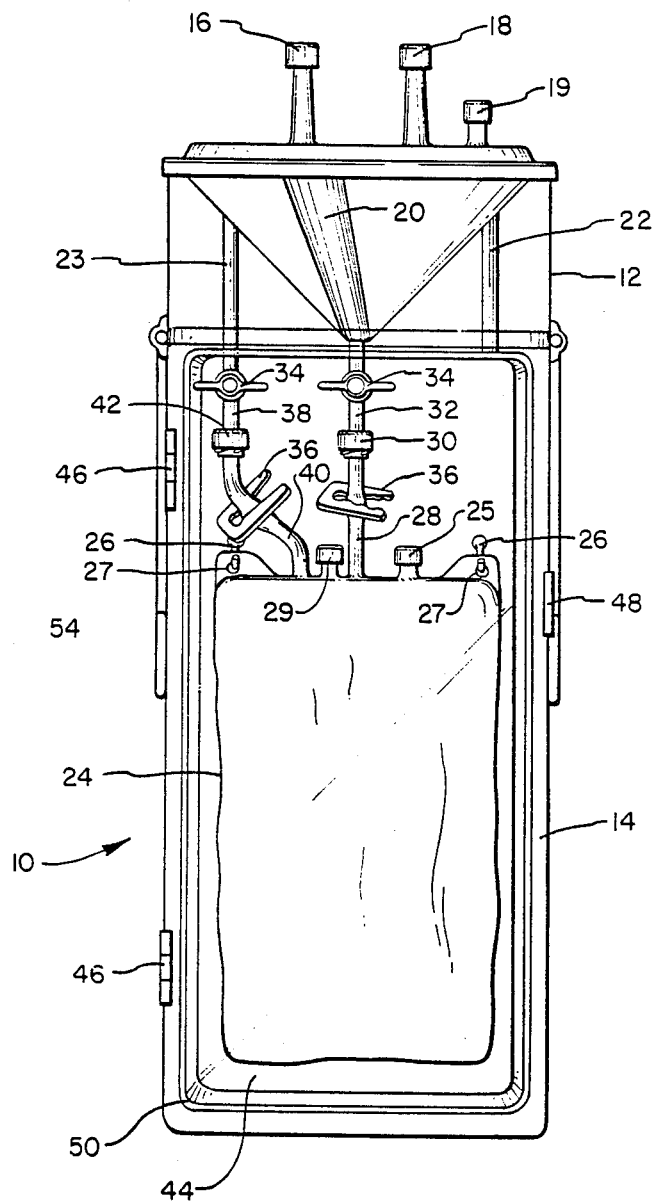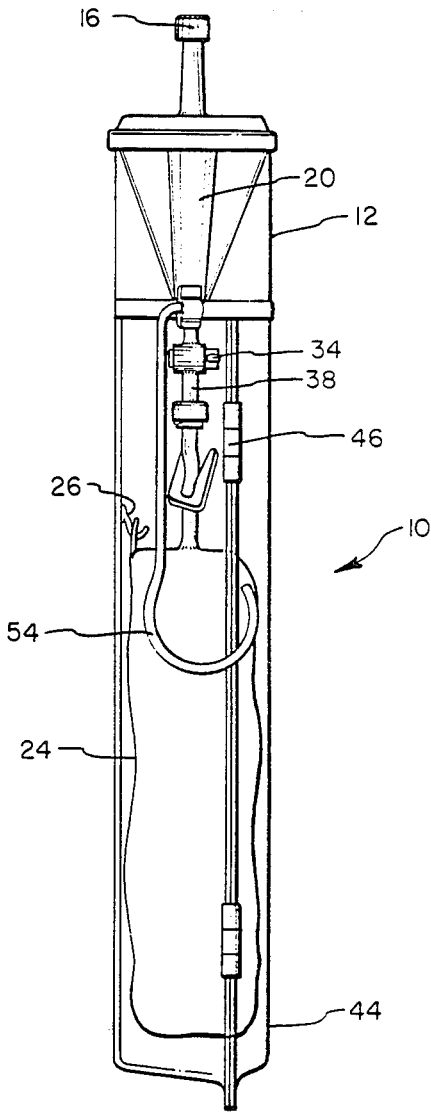
FIG. 1
FIG. 2

AUTOLOGUS BLOOD METHODS AND APPARATUS

RELATED APPLICATIONS

This application is a continuation-in-part application of copending application Ser. No. 06/928,928, filed Nov. 7, 1986, and entitled METHODS AND APPARATUS FOR AUTOTRANSFUSION OF BLOOD, which application is incorporated herein by this reference.

BACKGROUND

1. The Field of the Invention

The present invention relates to methods and apparatus for use in the autotransfusion of blood. More particularly, the present invention relates to an improved autotransfusion system which minimizes the amount of air in contact with the blood such that hemolysis is minimized.

2. The Background of the Invention

It has generally been accepted in the art that when dealing with a situation in which a person loses a significant quantity of blood, it may be necessary to transfuse homologous blood to the individual as part of the individual's treatment. That is, blood from a donor is injected into the patient's system in order to compensate for blood lost.

It will be readily appreciated that blood transfusions are generally required in several different definable contexts. For example, a serious trauma and resulting loss of blood may dictate that additional blood be transfused to the patient as a part of the patient's treatment. Similarly, in the context of serious and traumatic surgery, such as heart surgery, it is generally necessary to add blood to the patient's system to make up for blood loss during the surgical procedure.

In the case of both surgery and trauma, additional blood loss will at times be encountered during the recovery period. As a result, it is possible that the blood lost following surgery or trauma may require replacement. Traditionally, in each of these settings, replacement blood is obtained from a donor and then injected into the patient using various known techniques depending on whether the patient is at that time undergoing surgery or is recovering postoperatively.

Several problems have recently developed in the general area of transfusing blood. One such problem is that donor blood is becoming more and more scarce. With the increase in demand for homologous blood there has been a corresponding decrease in the amount of donor blood available. As a result, it is at times difficult to obtain the blood necessary to complete needed transfusions. In the event blood is found available, the cost of that blood is generally quite great. Thus, a blood transfusion can add significantly to the cost of treating a patient.

Additionally, certain adverse reactions have been experienced when using homologous blood. For example, immune and allergic reactions are possible in certain cases. Such reactions can have serious adverse effects on a patient's recovery. Likewise, homologous blood can at times carry certain diseases.

For example, hepatitis is commonly transmitted through homologous transfused blood. There is also considerable concern about the transmission of other serious diseases, such as, for example, acquired immune deficiency syndrome (AIDS) and malaria.

As a result of the problems discussed above, the possibility of providing autotransfusion of autologous blood has received increasing attention. Autologous blood is generally comprised of blood lost or donated by the patient himself which is reintroduced into the patient as needed during the surgical procedure or the postsurgical recovery period.

It is interesting to note that autotransfusion was first discussed in the literature as early as 1818, and was strongly recommended at various times in the late 1800's. Since the introduction of the concept of autotransfusion, its popularity has varied. Because of the problems discussed above, however, interest in autotransfusion is now again on the increase.

Along with the increased interest in autotransfusion has come an increased number of studies on the feasibility of autotransfusion. In general, it is found that autotransfusion is a relatively effective way of providing transfused blood during surgical procedures, trauma, and the postsurgical recovery.

A problem which has existed in the art, however, relates to providing an effective and acceptable apparatus for collecting autologous blood and reinfusing that blood into the patient. In attempting to provide such an apparatus, a variety of systems and blood collection containers have been developed. Generally, the containers are designed for use with shed mediastinal or thoracic blood. Blood from these sources, of course, is collected during cardiac surgery or after severe trauma to the chest region.

Most of the known devices for use in autotransfusion are simple containers. In addition, it has been quite popular in the past to provide a container which is placed in communication with a source of vacuum. As a result, the blood is drawn into the container from the surgical or trauma area.

Some containers of this general sort have been modified by placing disposable liners within the interior of the container and then providing a vacuum to drive the blood into the disposable liner. This type of container, however, is conventionally used to collect blood and other fluids for disposal rather than reinfusion.

In certain instances it has been found necessary to separate non-blood fluids from the blood collected. As a result, certain containers have been developed which have a collection container for blood and a separate collection container for other types of fluids. These containers, however, operate on the same general principle of simply sucking fluid into the container under vacuum.

While various configurations of devices have been developed, the basic principles of operation have essentially remained the same. That is, blood is forced into the device under a high vacuum with a large air flow across the blood-air interface. The collection device is simply a container used to collect the blood. Once the blood is collected within the container, it is then either immediately reinfused, transferred to a separate container and then reinfused, or discarded.

It will be appreciated that one of the serious problems in the art, particularly when using flexible or collapsible containers, is with respect to maintaining the container in an open position so that the blood can flow into the container. Some existing containers have been either mechanically opened using stays or they have been opened by using a high external vacuum.

The result of maintaining the flexible container in the open position is, however, that blood flowing into the container will contact and mix with air as it is collected. It is well known in the art that the mixing of blood and air can result in severe hemolysis, fibrin clotting, and/or the production of emboli including air emboli.

It can be appreciated from the above discussion that one of the severe problems in prior art devices is the damage to the blood collected. As mentioned above, this damage may take the form of hemolysis, clot formation, or "drying" of the blood as it is collected. One of the factors in causing the damage to the blood is the high vacuum under which the many of existing devices operate, coupled with extensive mixing between air and blood within the system. This mixing results in damage to the blood, rupture of blood cells, and protein denaturation.

Another problem in existing autotransfusion systems is in providing adequate filtering of the blood once it is collected. As can be appreciated from the discussion above, it is not unusual for emboli to be found within collected blood. As a result, it is critical that adequate filtering be provided. Most of the prior art devices, however, have difficulty providing necessary blood filtering.

A further problem which has arisen in the art is that the blood collection devices are not of a conventional uniform type. That is, operating room and other medical personnel are not generally familiar with the devices and with their operation. Such lack of familiarity with the collection device can lead to an increased possibility of technical error in the collection and reinfusion of blood.

Similarly, many prior art devices fail to provide adequate visual monitoring of the collection and reinfusion procedure. This is generally caused by opaque portions of the device obstructing the view of the technician. This also results in less than ideal conditions under which to collect autologous blood and additional technical difficulty in operating the device.

It is apparent that what is needed in the art are methods and apparatus for easily and effectively collecting blood for autotransfusion purposes. Specifically, it would be an advancement in the art to provide methods and apparatus for collecting autotransfusion blood which avoided the problems discussed above. It would also be an advancement in the art to provide such methods and apparatus which minimize the air-blood interfaces during blood collection and collected blood into a collapsed blood bag.

It would be a further advancement in the art to provide an apparatus which employed a conventional blood transfer bag. It would be a related advancement in the art to provide such an apparatus which was capable of using a series of conventional blood transfer bags to collect the desired volume of blood. It would also be an advancement in the art to provide such an apparatus which provided for easy visual monitoring of the operation of the device. Such methods and apparatus are disclosed and claimed below.

BRIEF SUMMARY AND OBJECTS OF THE INVENTION

The present invention is directed to improved methods and apparatus for the collection of blood to be used for autotransfusion purposes. The present invention overcomes the limitations and problems in the prior art which were discussed above. In particular, the present invention provides a system which operates at either high or low vacuum or through hydrostatic pressure and yet minimizes the air-blood interfaces and provides for early debubbling of the blood collected.

One embodiment of the present invention employs two main compartments. The apparatus includes an upper reservoir wherein the collected blood enters the device. A lower container is placed in fluid communication with the upper reservoir. Disposed within the interior of the container is a conventional blood bag which is in turn placed in fluid communication with the upper reservoir. If the device is to be used under the relatively high vacuum condition of the operating room, the device may also include a separate air-blood separator.

The upper reservoir has two external connections. The first connection is for receiving blood from the patient directly or by way of the air-blood separator. The connector can be of any type used for receiving the type of tubing used in operating room suction systems.

A filtering structure may be disposed within the upper reservoir and be connected directly to the inlet connection from the patient. The filtering mechanism provides for early debubbling of the blood flowing into the device and also filters out any emboli or cell masses which may have developed in the collection process. Once the blood is collected within the upper reservoir it flows out of the upper reservoir into the container and subsequently into the blood bag.

The second external connection places the upper reservoir in communication with a source of vacuum. It is expected that the present invention will operate easily with a source of either high or low vacuum or possibly without any vacuum at all using simply the hydrostatic head developed by the collection of the blood. In any event, the upper reservoir is supplied with a connector capable of placing the upper reservoir in communication with a vacuum system such as the surgical suction system.

The lower container and the interior of the blood transfer bag are also placed in communication with the vacuum source of the reservoir. As a result, there is a pressure equalizing feature inherent within the device when used alone or when used in connection with an air-blood separator. One of the benefits of this feature is that it allows the blood to continue to flow through the device into the blood bag without extending or opening the blood bag. As a result, there is no air-blood interface as the blood enters the blood bag.

As discussed above, a conventional blood transfer bag may be disposed within the lower container. The inlet from the blood transfer bag is attached to the base of the reservoir and receives blood which has settled into the reservoir. Various stopcocks, shutoff valves, clamps, or other types of on-off valves, may be provided on the tubing which places the blood bag in communication with the reservoir.

A second tube from the blood bag will connect the interior of the blood bag to the upper reservoir. Again, the purpose of this line is to equalize the pressure throughout the device. In addition, as with the inlet line, the air vent or vacuum line may be provided with various on-off valves, such as stopcocks and clamps and the like, as needed or desirable in order to allow the mechanism to operate.

Even though the blood transfer bag is disposed within an enclosed container, the container is easily opened so that the blood bag can be removed and an additional blood bag inserted in its place. It will be appreciated that various stints and the like may be located within the container in order to hold the blood bag in place. When it is desired to use the blood collected in the autotransfusion apparatus, it is simply necessary to open the door of the container, remove the blood bag, and then reinfuse the blood into the patient.

In an additional embodiment of the invention, the upper reservoir and lower container are eliminated so that the device is comprised of the blood transfer bag and the other connecting structures described. This embodiment will likely include an air-blood separator placed on the inlet line from the patient. A filter may be disposed within the air-blood separator so that blood entering the air-blood separator is immediately filtered. The filtered blood then leaves the air-blood separator through a feed line. The feed line from the separator is in turn connected directly to a blood transfer bag.

The interior of the blood transfer bag is also placed in direct communication with the vacuum line leaving the air-blood separator by way of a vacuum return line. Thus, the pressures throughout the system are equalized. Furthermore, any air which may make its way into the blood transfer bag is easily removed through the vacuum return line. This allows the device to operate with minimized air-blood interaction.

It will be appreciated that the present invention in each of its embodiments reduces hemolysis and other types of cell damage. The device minimizes the air-blood interfaces and provides for the early separation of air from the blood. Thus, the major cause of blood damage in prior art devices is greatly reduced.

It is, therefore, an object of the present invention to provide an autotransfusion device which is capable of operating at low vacuum, high vacuum, or through hydrostatic (gravity) feed while minimizing blood damage.

It is a further object of the present invention to provide an autotransfusion system which minimizes air-blood interfaces within the device and also provides for the early debubbling of blood flowing through the device.

Another object of the present invention is to provide an autotransfusion system which employs conventional blood transfer bags which are typically used in the art.

It is a related object of the invention to provide an autotransfusion system which can be used repeatedly with a series of different blood bags.

It is still another object of the present invention to provide an autotransfusion system whereby the operation of the system can be monitored visually.

These and other objects of the invention will become apparent upon reading the following detailed description and appended claims and upon reference to the accompanying drawings.

BRIEF DESCRIPTION OF THE DRAWINGS

FIG. 1 is a front plan view of a first embodiment within the scope of the present invention.

FIG. 2 i a side plan view of the embodiment of the present invention illustrated in FIG. 1.

FIG. 2 is a side plan view of the embodiment of the invention which operates without the need of upper reservoir or container.

DETAILED DESCRIPTION OF THE PREFERRED EMBODIMENTS

Figure 3:
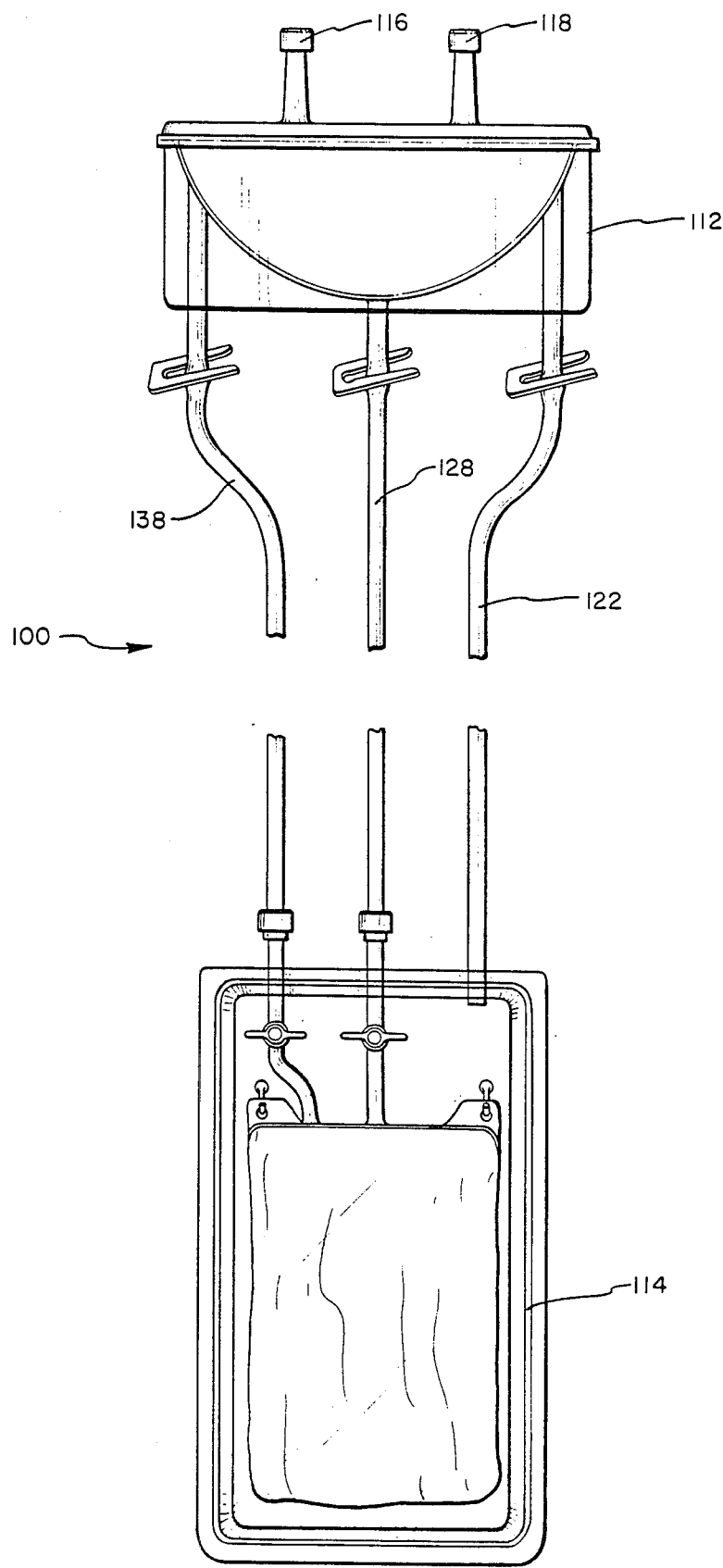
FIG. 3 is a front plan view of a second embodiment within the scope of the present invention.

The present invention can be best understood by reference to the drawings, wherein like parts are designated with like numerals throughout. Referring more particularly to FIG. 1, a first embodiment within the scope of the present invention is illustrated. The autotransfusion device of the present invention is generally designated 10 in FIG. 1. The autotransfusion device 10 is particularly adaptable for use in collecting and processing blood from a patient. Once the blood is fully collected within the device 10, the blood is generally suitable for reinfusion into the patient from which the blood came originally.

Also illustrated in FIG. 1 are the two basic components of the device 10. These components include upper reservoir 12 and container 14. With respect to the upper reservoir 12, at least two inlet or connector means are disposed within the top of upper reservoir 12 as illustrated in FIG. 1. In particular, upper reservoir 12 includes a blood inlet connector 16 and a vacuum connector 18. Also disposed within upper reservoir 12 is a port 19 through which anticoagulants or other medications may be added to the collected blood.

In the embodiment of the device illustrated in FIG. 1 a tubular filter 20 is connected to blood inlet connector 16 and is then run to near the base of upper reservoir 12. Tubular filter 20 acts to remove emboli, air bubbles and the like from the blood immediately upon collection.

It will be appreciated that blood inlet connector 16 and vacuum connector 18 may be configured so that they are easily connectable to standard tubing used in operating room vacuum systems. As a result, in order to place the device 10 in operation it is simply necessary to connect a length of tubing (not shown) to blood inlet connector. The tubing will then run to the patient in order to receive the autologous blood. At the same time, a length of tubing may be connected to vacuum connector 18 and then run to a source of vacuum within the operating room. The source of vacuum may be the operating room suction system or the vacuum system within a patient's hospital room.

Also illustrated in FIG. 1 are vacuum ports 22 and 23 which are disposed through portions of upper reservoir 12. As illustrated in FIG. 1, it can be seen that vacuum ports 22 and 23 place upper reservoir 12 in communication with the interior of container 14 and also blood transfer bag 24. The function of vacuum ports 22 and 23 will be discussed in more detail below.

It will be appreciated that the primary function of upper reservoir 12 is to provide a collection reservoir for blood flowing into the device. Blood flowing into the device through blood inlet connector 16 will be immediately filtered and debubbled by filter 20. Filter 20 may take a variety of configurations, and the filter configuration illustrated in FIG. 1 is but one illustrative possibility. As a result, blood flowing into the device is treated immediately in order to remove emboli and air bubbles. This prevents further hemolysis or damage to the blood and places the blood in condition to be transferred to a blood transfer bag and eventually reinfused back into the patient.

Also illustrated in FIG. 1 is the blood transfer bag 24 and the mechanism related to the operation of blood transfer bag 24. It will be appreciated that blood transfer bag 24 can be suspended within container 14 in any desired manner. For example, stints 26 are disposed through holes 27 in a portion of the blood transfer bag and are then anchored securely into the body of container 14. As a result, blood transfer bag 24 is held sufficiently securely within container 14 to allow for proper operation of the device.

Conventional blood transfer bags such as that illustrated in FIG. 1 may have a plurality of connectors and parts. For example, blood transfer bag 24 has a port 25 through which anticoagulants or other medications can be added to the collected blood. In addition, blood transfer bag 24 also has a reinfusion port 29. Reinfusion port 29 is adaptable for connection to a conventional reinfusion set in order to transfuse blood contained within blood transfer bag 24 back to the patient.

A length of tubing 28 extends upwardly from the top of blood bag 24 and then terminates at a connector 30. Extending downwardly from the upper portion of container 14 is a second length of tubing 32. Tubing 32 also terminates at connector 30 where it is placed in fluid communication with tubing 28.

It will also be appreciated from FIG. 1 that one or more on-off valves such as stopcocks 34 or slide clamps 36 may be placed along the length of tubing 28 and 32. Stopcocks 34 and slide clamps 36 will allow the flow of blood into the blood bag to be adequately controlled and will also provide for clamping off tubing 28 when it is desired to remove blood bag 24 from the device for reinfusion of the accumulated blood. It will be appreciated that a variety of known valves or clamps could be substituted for stopcocks 34 and slide clamps 36.

The entire mechanism comprising tubing 28, connector 30, tubing 32, stopcock 34 and slide clamp 36 serves to place the interior of blood transfer bag 24 in communication with the base of upper reservoir 12. As a result, blood collected in upper reservoir 12 will continue to flow downwardly into blood transfer bag 24 through the tubing, connectors, and valves.

Also illustrated in FIG. 1 is a vacuum or air vent mechanism between the body of upper reservoir 12 and blood transfer bag 24. The air or vacuum vent system of the device is similar in construction to the blood inlet means which runs between the upper reservoir 12 and the blood transfer bag 24.

Specifically, the air or vacuum vent may be comprised of two lengths of tubing 38 and 40. Again, a plurality of stopcocks 34 and slide clamps 36 or other mechanisms may be placed on the length of tubing 38 and tubing 40. The two lengths of tubing are held in place by a connector 42. Finally, tubing 38 is placed in communication with vacuum port 23 which leads to the upper portion of upper reservoir 12. As a result, the interior of blood transfer bag 24 will be placed in communication with the source of vacuum by way of vacuum connector 18.

The interior of container 14 is also placed in fluid communication with upper reservoir 12 through vacuum port 22. Vacuum port 22 assures that pressures within upper reservoir 12 and within container 14 remain approximately equal. At the same time, the interior of blood bag 24 is also placed in communication with upper reservoir 12 through vacuum port 22 by the mechanism discussed above. Thus, it will be appreciated that there will be equalized pressure among upper reservoir 12, container 14, and blood bag 24.

In order to maintain sterile conditions within the system during the period of time when blood transfer bags are replaced and container 14 is open, it may be desirable to place filters (not shown) within the interior of vacuum ports 22 and 23 to prevent contaminants from reaching the blood supply within upper reservoir 12. Such filters may, for example, be conventional hydrophobic filters.

As a further matter as mentioned above, it will periodically be necessary to open the interior of container 14 in order to remove a blood bag which is full and to replace the full bag with an empty blood bag. The embodiment of the device illustrated in FIG. 1, therefore, includes a door 44 disposed over the front of container 14. Door 44 is held to the remaining structure of container 14 by hinges 46. Furthermore, it may be desirable to place a handle 48 on the door 44 to aid in opening and closing door 44.

It will be appreciated that since the device operates under vacuum it is necessary to tightly seal the interior of container 14. As a result, as illustrated in FIG. 1, an O-ring 50 may be placed around the circumference of door 44 so that door 44 fits snugly within the remainder of container 14.

It is also important to note that the entire device may be disposable. As a result, the device and all of its components can be sterilized in advance and then simply discarded after use.

The operation of the device 10 can be easily appreciated from FIG. 1. A length of inlet tubing is connected from the patient to blood inlet connector 16 either directly or by way of an air-blood separator which will be discussed more fully below. At the same time vacuum connector 18 is connected to a source of vacuum which may be the operating room general vacuum system or the general suction system in a patient's hospital room. Blood transfer bag 24 is disposed within the interior of container 14.

As illustrated in FIG. 1, the various lengths of tubing 28, 32, 38, and 40 are placed in position as illustrated using connectors 30 and 42, stopcocks 34, slide clamps 36, or other on-off valves. Door 44 is then closed and secured so that a vacuum tight seal is provided.

Once the source of vacuum begins to take effect it will be appreciated that both upper reservoir 12 and container 14 are equally evacuated. As discussed above, container 14 is evacuated through vacuum port 22 which places upper reservoir 12 in communication with container 14. Likewise, the interior of blood bag 24 is evacuated by way of vacuum port 23. As a result, the entire device is placed under similar pressure conditions and no extreme vacuum conditions are produced at any point in the operation of the device.

When the device is properly prepared and connected, blood will begin to flow through blood inlet connector 16 and be filtered by filter 20. Blood will accumulate in upper reservoir 12 until a sufficient hydrostatic head is built up so that the blood will begin to flow through tubing 28 and 32 into the interior of blood transfer bag 24.

Blood transfer bag 24 will be essentially closed as the blood begins to flow into the blood transfer bag 24. As a result, there is no additional air-blood interface between upper reservoir 12 and blood transfer bag 24, which interfaces are known to cause hemolysis and other damage to the blood.

It may be preferable to construct the entire device from a clear material such as a clear plastic. When constructed of a clear material, the operation of the device 10 can be easily monitored visually by a technician. In particular, the filling of blood bag 24 may be monitored. As a result, when blood transfer bag 24 is sufficiently full, door 44 may be opened, stopcocks 34 and slide clamps 36 may be closed, and the blood transfer bag can be disconnected at connectors 30 and 42.

Once the blood bag 24 is disconnected, it can be removed and replaced with a new empty blood transfer bag. The full blood transfer bag can then be transported to the patient where the blood in the blood transfer bag 24 can be reinfused. Meanwhile, the new blood bag 24 can be easily inserted into the container 14, the stopcocks 34 and slide clamps 36 can be opened, and the operation of the device can be continued. As noted above, when the use of the device 10 is completed, the entire apparatus can be discarded.

FIG. 2 illustrates the side of device 10. The primary additional feature illustrated in FIG. 2 is a handle 54 which can be used to hang the device 10 in a convenient position. This handle can be configured so as to make the device readily usable in a surgical setting.

FIG. 3 illustrates an alternative embodiment of the device. In particular, the device in FIG. 3 is generally designated 100. In the embodiment illustrated in FIG. 3 the upper reservoir 112 and the lower container 114 are not securely connected, but rather are placed in communication by a plurality of tubes whose functions are more fully described below.

The upper reservoir 112 of the device 100 includes a blood inlet connector 116 and a vacuum connector 118. Other than the fact that upper reservoir 112 is disconnected from container 114, upper reservoir 112 has essentially the same characteristics and method of operation as does upper reservoir 12.

Upper reservoir 112 is, in turn, connected to container 114 through a series of elongated tubes. The center elongated tube 128 is used to carry blood from upper reservoir 112 to container 114, whereas tube 138 places the interior of blood transfer bag 124 in vacuum communication with upper reservoir 112.

The operation of the device illustrated in FIG. 3 is similar to that of the device illustrated in FIG. 1, with the exception that upper reservoir 112 is not secured to the container 114. This feature allows upper reservoir 112 to be placed very near to the site where blood is collected.

As with the previously described embodiment of the device, the time period during which there may be air within the blood collected is minimized in that blood is introduced into upper reservoir 112 and filtered immediately upon collection. Furthermore, the time between the entry of blood into the system and its collection in upper reservoir 112 is minimized by placing the upper reservoir 112 very near the surgical site. As a result, hemolysis and the possibility of producing emboli may be reduced when upper reservoir 112 is mobile and can be placed very close to the blood collection location.

It will also be appreciated that the device illustrated in FIG. 3 operates under the same principles as that illustrated in FIG. 1. In particular, the interior of container 114 is placed in vacuum communication with upper reservoir 112 by way of tube 122. At the same time, the interior of the blood transfer bag 124 is placed in communication with the same source of vacuum by way of tube 138. As a result, blood is collected using the same techniques described above.

Figure 4:
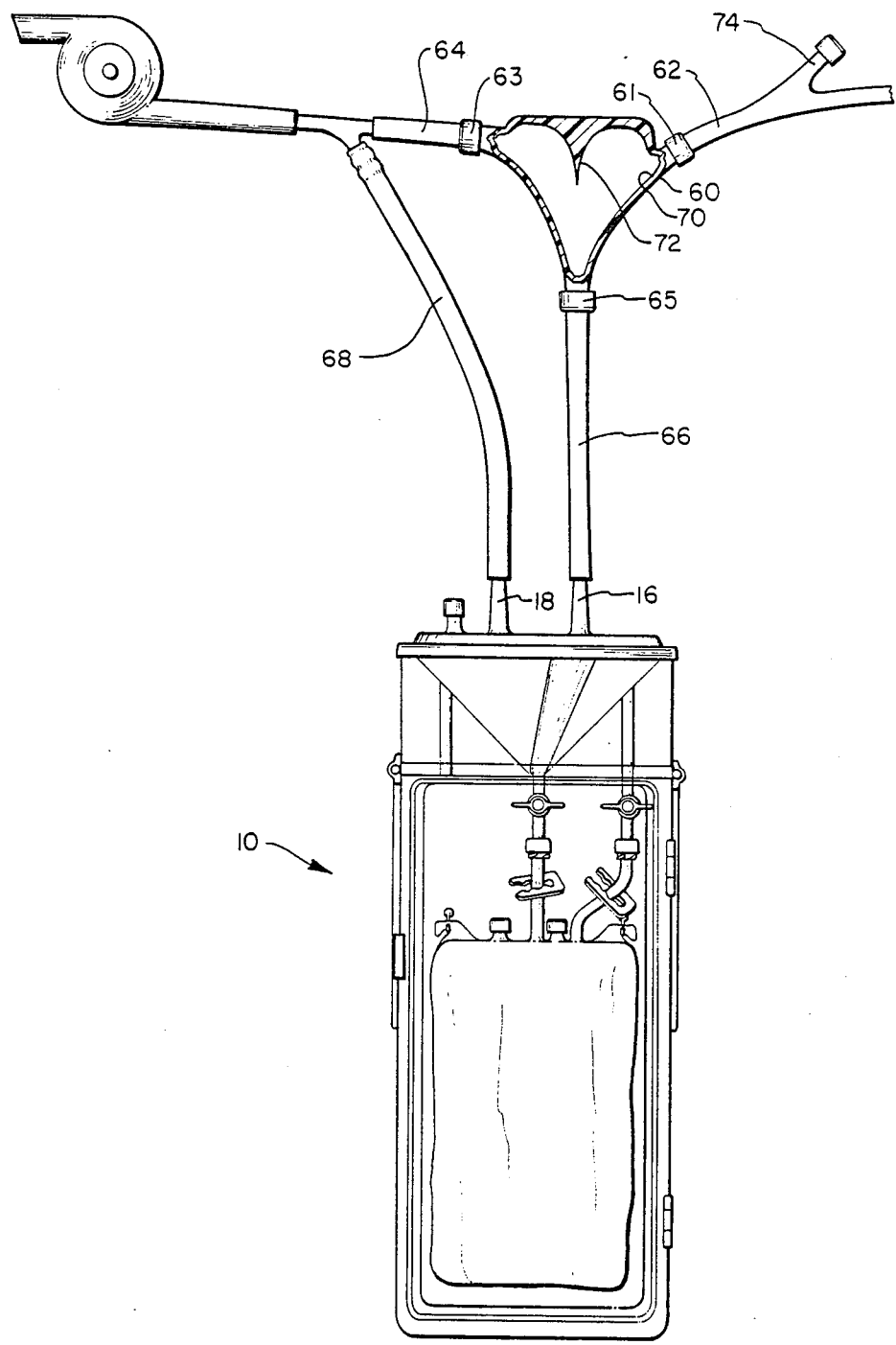
FIG. 4 is a front plan view of a further embodiment of the device.

FIG. 4 illustrates the device 10, described with reference to FIGS. 1 and 2 above, in use in a high vacuum surgical setting. FIG. 4 illustrates a system which includes an air-blood sesparator 60. The air-blood separator 60 as illustrated in FIG. 4 includes three connections. These connections include a connection 61 capable of being attached to a source of blood, a connection 63 capable of being attached to a source of vacuum, and feed line connection 65 capable of being connected to a line which is in communication with device 10.

Air-blood separator 60 is in turn connected to an inlet line 62 using connection 61 and a vacuum line 64 using connection 63. In addition, air-blood separator 60 is attached to feed line 66 which leads to the device 10 by way of connection 65.

Also included within the system shown in FIG. 4 is vacuum return line 68. Vacuum return line 68 serves to equalize pressure throughout the system as described above with reference to FIG. 1. This is accomplished because vacuum return line 68 is in communication with vacuum line 64 which in turn places the entire system in communication with a source of vacuum. Thus, the same pressure conditions which exist in vacuum line 64 are communicated to air-blood separator 60 as well as throughout device 10.

It will be appreciated with respect to FIG. 4 that the interior wall 70 of air-blood separator 60 has a very gentle slope. As a result, blood flowing into air-blood separator 60 through inlet line 62 will descend gently along the gently sloping interior wall 70. It is expected that the slope of interior wall 70 will further aid in minimizing the damage to blood flowing into the device.

Also illustrated in FIG. 4 is a baffle 72. Baffle 72 is used to assure that no blood flowing into air-blood separator 60 through inlet line 62 is then sucked out of the separator through vacuum line 64 into the vacuum system.

Blood flowing into the air-blood separator 60 by way of inlet line 62 then travels along the gently sloping wall 70 until it reaches the general area of feed line connection 65. At this point, the blood will exit air-blood separator 60 through feed line 66 which is in turn attached to blood inlet connector 16 of device 10.

An additional illustrated feature of the system is an anticoagulant injection line 74. The placement of anticoagulant injection line 74 allows anticoagulant or other medications to be added to the blood to the extent desired at a point very early in the collection process.

As mentioned above, pressures within the system illustrated in FIG. 4 will be equalized throughout. This is accomplished by connecting the collection device 10 to the vacuum line 64 by way of vacuum return line 68. Thus, the interior of container 14, blood transfer bag 24, and upper reservoir 12 are all placed in communication with the same source of vacuum as that which drives the system as a whole.

Even though the system illustrated in FIG. 4 may operate at relatively high vacuum, the disadvantages encountered in the existing art are avoided. In particular, air is removed from the blood early in the collection process as it flows into air-blood separator 60. A solid column of blood can then be created as the blood leaves air-blood separator 60 by way of feed line 66. This early air-blood separation and debubbling largely avoids the hemolysis encountered in conventional devices.

Figure 5:
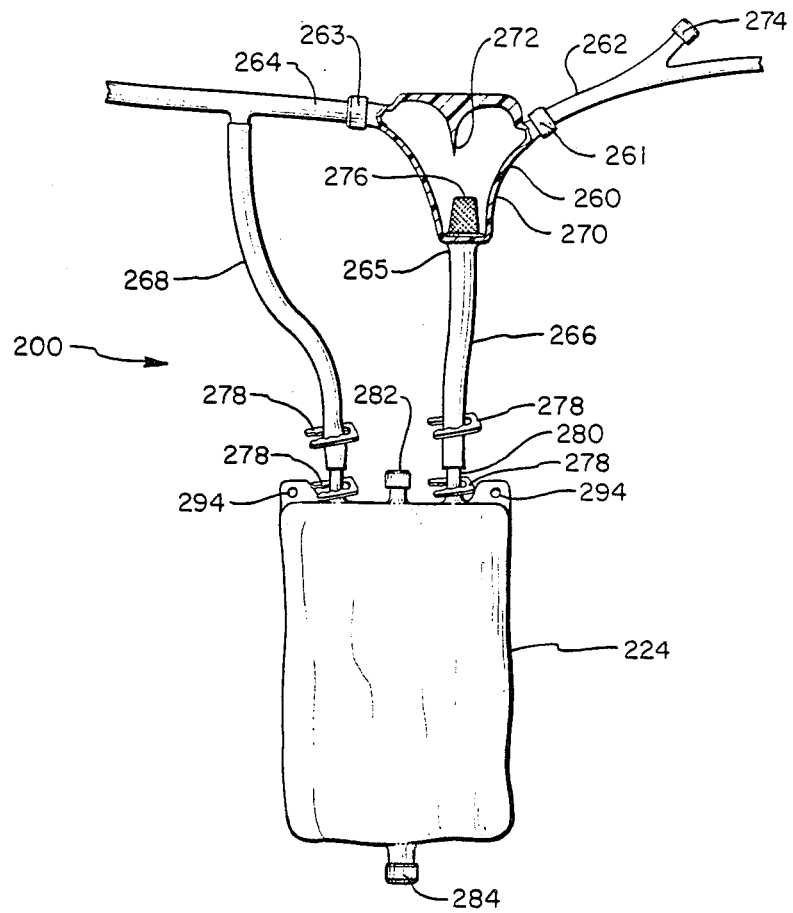

FIG. 5 illustrates an additional embodiment of the present invention. In the embodiment illustrated in FIG. 5, the upper reservoir and container sections, as described above, are eliminated. The device 200 is able to operate by using an air-blood separator 260 and a blood transfer bag 224 without many of the structural features described above.

The air-blood separator 260 as illustrated in FIG. 5 may be of the same type as that used in the embodiment illustrated in FIG. 4. The air-blood separator 260 is connected to an inlet line 262 at a connection 261. Inlet line 262 may also include an anticoagulant injection port 274. Air-blood separator 260 is also connected to vacuum line 264 at connection 263.

The structure of air-blood separator 260 itself is also similar to that of air-blood separator 60 described above. This structure includes an interior wall 270 which allows blood to flow smoothly through the system, as well as an optional interior baffle 272. Also disposed within the interior of separator 260 is a filter 276. Filter 276 provides immediate filtering of blood which flows into separator 260 before that blood is able to leave the separator. Thus, there is no need for additional blood filters at other points within the device.

The separator 260 is also attached to feed line 266 at a point of attachment or connection 265. Feed line 266 is in turn attached to a blood transfer bag 224 of the type described above. Clamps 278 or other means of closing the subject openings and tubing may be disposed along feed line 266 and in the area of the connection 280 between blood transfer bag 224 and feed line 266.

Blood transfer bag 224 is also placed in communication with vacuum line 264 by means of a vacuum return line 268. Again clamps 278 or other means of closing the subject openings and tubing may be disposed along vacuum return line 268 and in the area of connection 282 between blood transfer bag 224 and vacuum return line 268.

Also illustrated in FIG. 5 is a medication injection port 282 and a blood remove port 284. Thus, anticoagulants or other medications can easily be added to the blood collected at any desired time. In addition, blood can easily be removed through blood removal port 284 when it is necessary to reuse the blood collected.

Figure 6:
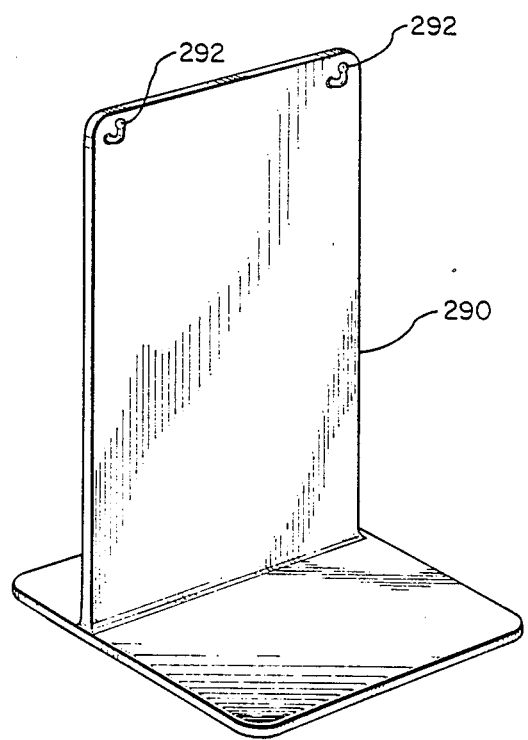
FIG. 6 is a perspective view of one embodiment of a rack for holding the blood transfer bag illustrated in FIG. 5.

It will be appreciated that the blood transfer bag 224 will require support during use. Stand 290, as illustrated in FIG. 6, can be provided to support the device. Blood transfer bag 224 can be hung on stand 290 by simply placing stints 292 into holes 294 in the blood transfer bag 224.

In use, vacuum line 264 will be placed in communication with a source of suction such as the vacuum system in an operating room or hospital room. Suction will thus be provided to inlet line 262 which will be placed in communication with the blood source. Blood will then flow into air-blood separator 260 and travel downwardly along interior wall 270. Baffle 272 will simultaneously prevent blood from continuing into vacuum line 264.

Blood will be filtered by filter 276 and then pass into feed line 266 and eventually enter blood transfer bag 224. Constant pressure will be maintained throughout the system with the help of vacuum return line 268. Vacuum return line 268 also assures that air entering blood transfer bag 224 will be immediately removed. Thus, air-blood mixing within blood transfer bag 224 is prevented. At the same time, autologous blood is collected at a very low cost due to the low cost of this particular embodiment of the invention.

In summary, it can be appreciated that the present invention accomplishes the objects which were set forth above. In particular, the present invention reduces hemolysis which is typically encountered in the surgical setting by early separation of any air contained within the blood. In addition, once the blood is introduced into the device, there are no further air-blood interfaces in that the blood bag is maintained in an essentially closed position. The device provides a smooth flow of blood into the blood bag under low vacuum. As a result, the major sources of hemolysis and blood damage encountered in the prior art are avoided.

As mentioned above, the present invention equalizes the pressures in all areas of the apparatus. As a result, the variations in pressure encountered in the conventional art are eliminated. In contrast to the existing devices, the present invention is able to employ the hydrostatic head produced by blood flowing within the device to aid in collection while avoiding the blood damage encountered in the prior art.

In addition, it will be appreciated that the blood is degassed and filtered immediately upon entry into the upper reservoir or alternatively upon entering the air-blood separator. This provides for immediate defoaming which minimizes any air related hemolysis or blood damage which may occur within the device.

The present invention employs a conventional blood transfer bag. The fact that a conventional blood bag is used will reduce the amount of training required to use the device and also will reduce the potential for technical errors.

It will further be appreciated that the present invention may be disposable and may be constructed of inexpensive and easily handled materials. The fact that the present invention is made of conventional and disposable materials provides for ease of operation and use by the medical personnel. In particular, the device may be sterilized in advance so that no sterilization is required prior to use in the hospital setting.

An additional feature of the present invention is the fact that the entire invention may be made of clear material. As a result, operation of the device can be readily observed without obstruction. This allows the medical technician to observe when the blood bag is full and requires replacement without allowing the device to back-up.

It will be appreciated that the apparatus and methods of the present invention are capable of being incorporated in the form of a variety of embodiments, only a few of which have been illustrated and described above. The present invention may by embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed and desired to be secured by United States Letters Patent is:

1. An apparatus for collecting blood from a patient for reinfusion comprising:
   means for separating air from the blood collected for reinfusion;
   first conduit means for conveying the blood collected from the means for separating air from the blood to a blood collection receptacle;

a blood collection receptacle having a blood inlet and a vacuum port, the blood receptacle being readily removably from the means for conveying the blood after receipt of blood and being capable of being maintained in a collapsed configuration prior to receipt of collected blood and the blood collection receptacle expanding from a collapsed configuration to an expanded configuration in relation to the amount of blood which has flowed into the receptacle and such that further contact between air and blood flowing into the receptacle is avoided; and second means for placing a source of vacuum in communication with the blood receptacle and the separating means.

2. An apparatus for collecting blood from a patient for reinfusion as defined in claim 1, further comprising a source of vacuum, said source of vacuum being placed in communication with the separating means and the blood receptacle, such that pressures within the apparatus are equalized.

3. An apparatus for collecting blood from a patient for reinfusion as defined in claim 2 wherein the second means for placing a source of vacuum in communication with the blood receptacle comprises a vacuum return line in communication with the receptacle at one end and in communication with the source of vacuum at the other end.

4. An apparatus for collecting blood from a patient for reinfusion as defined in claim 3 further comprising at least one clamp attached to the vacuum return line capable of closing said vacuum return line.

5. An apparatus for collecting blood from a patient for reinfusion as defined in claim 1 wherein said means for separating comprises an air-blood separator comprising a housing.

6. An apparatus for collecting blood from a patient for reinfusion as defined in claim 5 wherein the means for conveying blood collected comprises a feed line connected at one end to the air-blood separator and at the other end to the blood collection receptacle.

7. An apparatus for collecting blood from a patient for reinfusion as defined in claim 6 further comprising at least one clamp attached to the feed line capable of closing said feed line.

8. An apparatus for collecting blood from a patient for reinfusion as defined in claim 1 wherein said air-blood separator comprises a base and a connection capable of being attached to a blood supply, a connection capable of being attached to a source of vacuum and a connection, near the base of the separator, capable of being attached to the means for conveying blood to the receptacle.

9. An apparatus for collecting blood from a patient for reinfusion as defined in claim 8 wherein the air-blood separator further comprises a baffle disposed within its interior such that blood flowing into the separator is prevented from flowing out through the vacuum connection.

10. An apparatus for collecting blood from a patient for reinfusion as defined in claim 8 wherein the air-blood separator further comprises at least one interior wall which gently slopes from the blood supply connection to the blood receptacle connection.

11. An apparatus for collecting blood from a patient for reinfusion as defined in claim 1 wherein the blood collection receptacle comprises a blood transfer bag having at least three openings therein.

12. An apparatus for collecting blood from a patient for reinfusion as defined in claim 1 further comprising means for supporting said blood receptacle.

13. An apparatus for collecting blood from a patient for reinfusion as defined in claim 12 wherein the means for supporting said blood receptacle comprises a stand to which the blood receptacle can be attached.

14. An apparatus for collecting blood from a patient for reinfusion as defined in claim 5 further comprising a blood filter disposed within said air-blood separator such that blood is filtered before it flows into said receptacle.

15. An apparatus for collecting blood from a patient for reinfusion as defined in claim 1 wherein the apparatus is comprised of a plastic material so as to be disposable after a single use.

16. An autologous blood collection apparatus as defined in claim 15 wherein the air-blood separator further comprises a baffle disposed within its interior such that blood flowing into the separator is prevented from flowing out through the vacuum connection.

17. An autologous blood collection apparatus comprising:

an air-blood separator comprising means for defining a chamber having a base, the air-blood separator further comprising a connection capable of being attached to a blood supply, a connection capable of being attached to a source of vacuum, a connection near the base of the separator capable of being placed in communication with a blood collection receptacle;

a blood collection receptacle having a blood inlet and a vacuum port, the blood collection receptacle capable of being maintained in a collapsed configuration prior to receipt of collected blood and expanding from a collapsed configuration to an expanded configuration relative to the amount of blood which has flowed into the receptacle, the blood collection receptacle being removable from the apparatus after receipt of the blood;

first conduit means for placing the blood collection receptacle in fluid communication with the air-blood separator;

second means for placing the blood collection receptacle in fluid communication with a source of vacuum; and means for removably and independently connecting the first conduit means and the second means to the blood collection receptacle.

18. An autologous blood collection apparatus as defined in claim 17 wherein said first conduit means for placing the blood receptacle in fluid communication with the air-blood separator comprises a feed line connected at one end to the air-blood separator and at the other end to the blood collection receptacle.

19. An autologous blood collection apparatus as defined in claim 17, further comprising a source of vacuum, said said source of vacuum being placed in communication with the air-blood separator and the blood collection receptacle, such that pressures within the apparatus are equalized.

20. An autologous blood collection apparatus as defined in claim 19 wherein the means for placing a source of vacuum in communication with the blood collection receptacle comprises a vacuum return line in communication with the receptacle at one end and in communication with the source of vacuum at the other end.

21. An autologous blood collection apparatus as defined in claim 17 wherein the air-blood separator further comprises at least one interior wall which gently slopes from the blood supply connection to the blood receptacle connection.

22. An autologous blood collection apparatus as defined in claim 17 wherein the blood collection receptacle comprises a blood transfer bag having flexible sides.

23. An autologous blood collection apparatus as defined in claim 17 further comprising a blood filter disposed within said air-blood separator such that blood is filtered before it flows into said receptacle.

24. A system for collecting blood from a patient for reinfusion to that patient comprising:

an air-blood separator comprising means for defining a chamber having a base and at least one interior wall, the air-blood separator further comprising a connection capable of being attached to a blood supply, a connection capable of being attached to a source of vacuum, a connection near the base of the separator capable of being attached to a feed line, wherein at least one interior wall of the air-blood separator gently slopes from the blood supply connection to the feed line connection;

a blood transfer bag which is capable of being maintained in a collapsed configuration prior to receipt of collected blood and capable of expanding substantially only enough to accommodate the amount of blood which has flowed into the blood transfer bag such that further contact between air and blood flowing into the receptacle is avoided;

means for removably holding the blood transfer bag stationary;

a feed line attached to the feed line connection of the air-blood separator at one end and removably attached to the blood transfer bag at the other end; and a vacuum return line removably attached to the blood transfer bag at one end and being capable of being placed in communication with the source of vacuum at the other end such that any air entering the blood transfer bag can be removed and such that pressures throughout the system are equalized.

* * * * *

UNITED STATES PATENT AND TRADEMARK OFFICE
CERTIFICATE OF CORRECTION

PATENT NO. : 4,775,360

DATED : October 4, 1988

INVENTOR(S) : Lane et al.

It is certified that error appears in the above-identified patent and that said Letters Patent is hereby corrected as shown below:

On the Title Page, Item [54], and Column 1, lines 1 and 2,
 in the Title, "AUTOLOGUS" should be --AUTOLOGOUS--
    Column 2, line 44, "dispoal" should be --disposal--
    Column 5, line 60, "i a" should be --is a--
    Column 5, line 66, FIG. 2 is a side plan view of the embodiment" should be --FIG. 5 is a front plan view of an embodiment--
    Column 12, line 46, "to back-up." should be --to back up.--
    Column 13, lines 2-3, "readily removably" should be --readily removable--
    Column 14, line 59, "said said" should be --said--

Signed and Sealed this

Thirteenth Day of June, 1989

Attest:

DONALD J. QUIGG

*Attesting Officer*    *Commissioner of Patents and Trademarks*